United States Patent
Friedman et al.

(10) Patent No.: US 8,617,197 B2
(45) Date of Patent: Dec. 31, 2013

(54) INTRODUCER DEVICE

(75) Inventors: Diana C. W. Friedman, Seattle, WA (US); Blake Hannaford, Seattle, WA (US); Devin Karns, Seattle, WA (US); Aylin Z. Kim, Seattle, WA (US); Louis Kim, Seattle, WA (US); Thomas S. Lendvay, Seattle, WA (US); Kristen S. Moe, Seattle, WA (US); James S. Pridgeon, Seattle, WA (US); Jacob Rosen, Santa Cruz, CA (US); Laligam Sekhar, Seattle, WA (US)

(73) Assignee: SPI Surgical, Inc., Seattle, WA (US)

( * ) Notice: Subject to any disclaimer, the term of this patent is extended or adjusted under 35 U.S.C. 154(b) by 91 days.

(21) Appl. No.: 13/051,888

(22) Filed: Mar. 18, 2011

(65) Prior Publication Data

US 2011/0257672 A1    Oct. 20, 2011

Related U.S. Application Data

(60) Provisional application No. 61/315,018, filed on Mar. 18, 2010.

(51) Int. Cl.
  *A61B 1/32* (2006.01)
  *A61M 29/02* (2006.01)
(52) U.S. Cl.
  USPC ............ 606/190; 600/207; 606/192; 606/198
(58) Field of Classification Search
  USPC ......... 606/108, 110, 113, 127, 128, 190–199, 606/205–209; 600/184, 201, 204, 207, 208, 600/224
  See application file for complete search history.

(56) References Cited

U.S. PATENT DOCUMENTS

| | | | | |
|---|---|---|---|---|
| 5,163,949 | A | * | 11/1992 | Bonutti .................. 606/192 |
| 5,373,854 | A | | 12/1994 | Kolozsi |
| 5,514,153 | A | * | 5/1996 | Bonutti .................. 606/190 |
| 6,179,776 | B1 | | 1/2001 | Adams et al. |
| 6,203,559 | B1 | * | 3/2001 | Davis et al. .............. 606/198 |
| 6,352,503 | B1 | | 3/2002 | Matsui et al. |
| 6,451,042 | B1 | * | 9/2002 | Bonutti .................. 606/190 |
| 2002/0128633 | A1 | | 9/2002 | Brock et al. |

(Continued)

FOREIGN PATENT DOCUMENTS

JP    2002-078772    3/2002

OTHER PUBLICATIONS

International Search Report and Written Opinion of PCT/US2011/029071 dated Nov. 23, 2011.

(Continued)

*Primary Examiner* — Kathleen Holwerda
(74) *Attorney, Agent, or Firm* — Wilson Sonsini Goodrich & Rosati

(57) ABSTRACT

An introducer and method provides a surgical tool with a pathway through tissue to a surgical site, wherein the surgical tool includes at least one surgical instrument. The introducer comprises a flexible sheath having a distal portion including a distal end and is arranged for receiving the surgical tool. A tissue separation tip at the distal portion of the sheath advances the sheath into the tissue towards the surgical site. The tissue separation tip is arranged to form a tissue gap and provide the at least one surgical instrument access to the tissue gap for performing a medical procedure consonant with the formation of the tissue gap or the performance of work at the surgical site.

23 Claims, 4 Drawing Sheets

(56) References Cited

U.S. PATENT DOCUMENTS

| | | |
|---|---|---|
| 2003/0013949 A1 | 1/2003 | Moll et al. |
| 2005/0085691 A1 | 4/2005 | Nakao |
| 2005/0137460 A1* | 6/2005 | Bertolero et al. ............ 600/213 |
| 2005/0206583 A1 | 9/2005 | Lemelson et al. |
| 2006/0052684 A1 | 3/2006 | Takahashi et al. |
| 2008/0058590 A1* | 3/2008 | Saadat et al. .................. 600/109 |
| 2009/0245600 A1 | 10/2009 | Hoffman et al. |

OTHER PUBLICATIONS

International Search Report and Written Opinion of PCT/US2011/029071 dated Dec. 12, 2011.

* cited by examiner

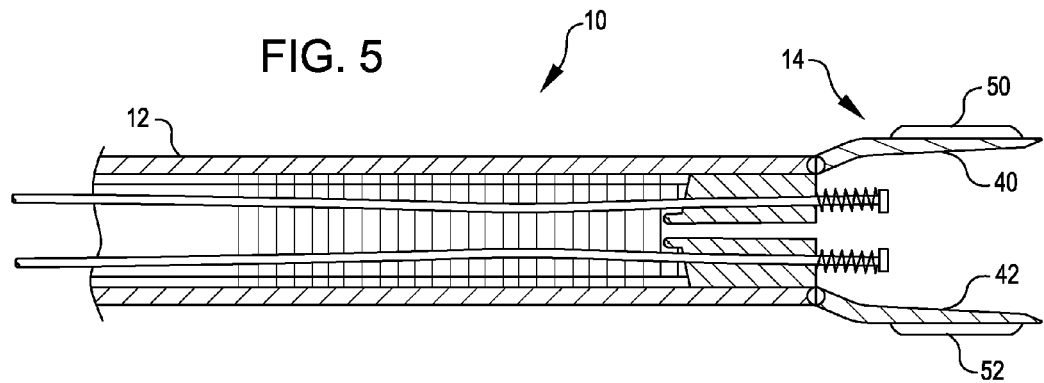
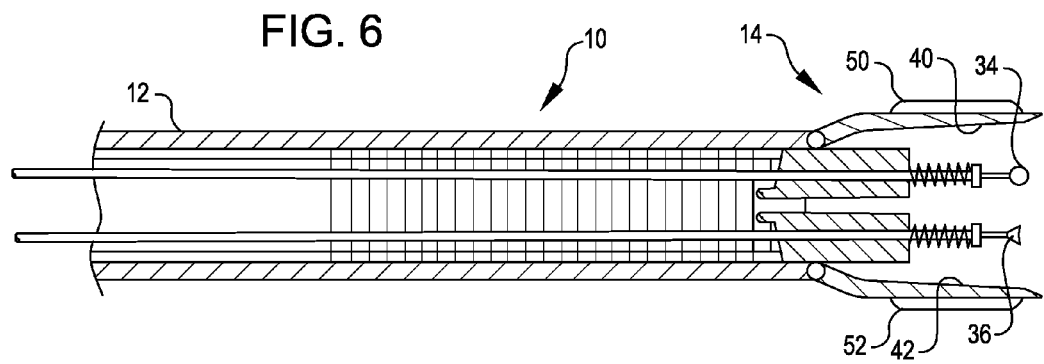
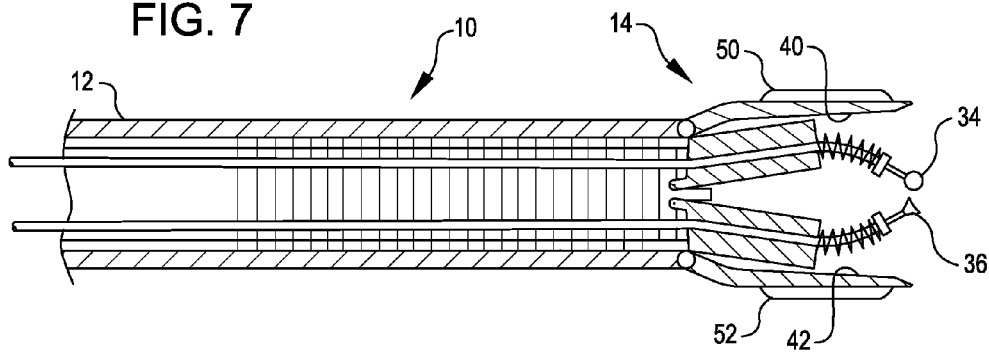

INTRODUCER DEVICE

PRIORITY CLAIM

The present application claims the benefit of copending U.S. Provisional Patent Application Ser. No. 61/315,018, filed Mar. 18, 2010; the foregoing application is incorporated herein by reference in its entirety.

BACKGROUND OF THE INVENTION

The present invention is directed to a surgical device. The present invention is more particularly directed to an introducer for providing a surgical tool with a pathway to a surgical site. The present invention is still more particularly directed to such an instrument for use with surgical devices for robotic surgery, such as for example, robotic neurosurgery.

Surgery has typically involved obtaining access to a region that exposes many aspects of a lesion (e.g. tumor, aneurysm, etc.) allowing its treatment or complete dissection and removal. However, obtaining access to the lesion may also involve damage to areas of the brain or other tissues that are normal. In view of the foregoing, a movement has developed to perform what is called "Minimally Invasive Surgery." Unfortunately, this, in many instances, is a misnomer since the surgery may or may not be "minimally invasive" both to the critical tissues under consideration, but also to collateral tissues at the site of entry or along the access path. A better term for this type of surgery is "Minimal Access Surgery." Examples of such surgery include: Endoscopic Surgery, Endoscope Assisted Surgery, Endovascular Surgery, Stereotactic Radiosurgery, etc.

It is often necessary to treat brain tumors and aneurysms in the base of the skull. These are very difficult to treat because accessing the skull base requires disruption of many important structures. It is desirable to minimize the size of any opening to be made through the skull and surrounding, healthy tissues so that pathology in the skull base is treated with the least amount of potential damage to surrounding tissues. Such a procedure could be thought of as "Minimally Disruptive Surgery." Current endoscopic and endoscope-assisted operations performed on the head, skull base, chest, abdomen, and other areas are done with rigid and straight endoscopes and tools that can only work in a straight line. However, in complex areas such as the brain, the endoscope has to negotiate many obstacles en route (e.g. bone, brain, and blood vessels). This imposes significant restrictions on the surgery being performed and can lead to an increase in collateral tissue damage, due to enlarging the access path and/or damaging or sacrificing the control over the structures near the lesion. Additionally, there are certain types of surgery that are at present not possible given the limitations posed by existing technology.

On the other hand, today's endovascular surgery is often performed over comparatively great distance, and by navigating through a variety of curved channels. Such surgery uses a system of coaxial tubes and actuation cables that work on the basis of forward and backward movement, and side-to-side movement. Such devices are used with real-time imaging that guides the operator to the target. A similar approach is used with flexible endoscopes that work inside the gastrointestinal tract. However, these methods are not applicable for micro scale surgeries, as are performed for intricate neurosurgeries.

In addition to the foregoing, it is sometimes desirable during surgical procedures to irrigate a surgical site, clean surgical tools, or repeatedly remove and re-introduce surgical tools. This presents a problem with currently known robotic surgical systems because removal of the entire system is generally required to change tools.

In answer to the short comings and problems associated with the surgical tools mentioned above, a new and improved surgical device has been under development. This device is shown and described, for example, in co-pending application Ser. No. 12/943,745(our 2915-001-03) filed Nov. 10, 2010, for SURGICAL DEVICE, which application is incorporated herein in its entirety. The surgical device describe therein is a surgical device capable of steering surgical tools to surgical sites over curvilinear neurosurgery paths to avoid unnecessary damage to sensitive or critical collateral tissue. The device is capable of steering surgical tools around anatomical obstacles while affording the tools complete maneuverability at the surgical site and removal/replacement during neurosurgical procedures.

While such a device represents a significant step forward for neurosurgical applications, the advancement would not be realized unless the surgical device could be delivered to the intended surgical site without causing damage to other tissue. What is thus required is an introducer that is capable of creating a working space for the surgical instrument by retracting adjacent tissue without causing undue trauma. For example, in neurosurgery, the introducer would need to be able to separate brain tissue from dura mater to create a channel to introduce the surgical tool. The tissue displacement must be both active and gentle. The introducer should desirably permit the surgical tools to be used during the surgical tool advancement procedure for visualization, connective tissue cutting and cauterizing in creating the instrument pathway and eventual surgical site. The present invention is directed to these and other issues.

SUMMARY

The invention provides an introducer for providing a surgical tool with a pathway through tissue to a surgical site, wherein the surgical tool includes at least one surgical instrument. The introducer comprises a flexible sheath having a distal portion including a distal end and is arranged for receiving the surgical tool. The introducer further comprises a tissue separation tip at the distal portion of the sheath for advancing the sheath into the tissue towards the surgical site. The tissue separation tip is arranged to form a tissue gap and provide the at least one surgical instrument access to the tissue gap for performing a medical procedure consonant with the formation of the tissue gap or the performance of work at the surgical site.

The tissue separation tip may comprise a plurality of fingers extending from and hingedly coupled to the sheath distal portion and be arranged to advance into the tissue when in a closed condition and to separate tissue to form the tissue gap when subsequently opened. The plurality of fingers may comprise at least two fingers. The introducer may further comprise a control cable for opening the fingers. The introducer may further comprise a control cable for closing the fingers. The introducer may further comprise an actuator associated with each finger, the actuators being operative individually or together for separate or concurrent opening of the fingers. The actuators may be operative in groups of two or more for opening different groups of the fingers by different amounts. The introducer may further comprise webbing bridging adjacent fingers to apply substantially uniform distributed pressure on the separated tissue.

The tissue separation tip may include a plurality of inflatable members which, when inflated, serve to separate the tissue and form the tissue gap. The introducer may further include at least one conduit communicating with the inflatable members for providing the inflatable members with an inflating fluid. The plurality of inflatable members may be arranged for individual or concurrent inflation. The plurality of inflatable members may be arranged for inflation of selected groups of two or more inflatable members.

The tissue separation tip may include a plurality of inflatable members which, when inflated, serve to separate the tissue and form the tissue gap. The inflatable members may be deflatable and the tissue separation tip may further include a plurality of fingers extending from and hingedly coupled to the sheath distal portion arranged to open as the inflatable members are deflated for maintaining the tissue gap formed by the inflatable members while also maintaining substantially constant pressure on the separated tissue. Each respective given one of the inflatable members may be carried by a respective given one of the fingers. The plurality of fingers may comprise at least two fingers and the plurality of inflatable members may comprise a like plurality of at least two inflatable members. The introducer may further comprise a control cable for opening the fingers. The introducer may further comprise a control cable for closing the fingers.

The introducer may further comprise a plurality of control cables. The control cables may be arranged for closing the fingers in selectable groups of two or more for concurrent closing of selected groups of fingers by differing amounts. The introducer may further comprise an actuator associated with each finger. The actuators may be operative individually or together for separate or concurrent opening of the fingers. The actuators may be operative in groups of two or more for opening different groups of the fingers by different amounts.

The introducer may further comprise webbing bridging adjacent fingers to apply uniform distributed pressure on the separated tissue. The introducer may further include at least one conduit communicating with the inflatable members for providing the inflatable members with an inflating fluid. The plurality of inflatable members may be arranged for individual or concurrent inflation or for inflation of selected groups of two or more inflatable members.

According to further aspects of the invention, an introducer provides a surgical tool with a pathway through tissue to a surgical site. The surgical tool includes at least one surgical instrument. The introducer comprises a flexible sheath having a distal portion including a distal end and arranged for receiving the surgical tool.

The introducer further includes a tissue separation tip at the distal portion of the sheath for advancing the sheath into the tissue towards the surgical site. The tissue separation tip is arranged to form a tissue gap and provide the at least one surgical instrument access to the tissue gap for performing a medical procedure consonant with the formation of the tissue gap. The tissue separation tip includes a plurality of inflatable and deflatable balloons which, when inflated, serve to separate the tissue and form the tissue gap and a plurality of fingers extending from and hingedly coupled to the sheath distal portion carrying the balloons and arranged to open as the balloons are deflated for maintaining the tissue gap formed by the inflatable members while also maintaining substantially constant pressure on the separated tissue.

According to further aspects of the invention, the invention provides a method of introducing a surgical tool to a surgical site within tissue, wherein the surgical tool includes at least one surgical instrument. The method comprises providing an introducer comprising a flexible sheath having a distal portion including a distal end and arranged for receiving the surgical tool and a tissue separation tip at the distal portion of the sheath, the tissue separation tip when in a first configuration being adapted for advancing the tip through the tissue and when in a second configuration adapted for separating the tissue. The method further includes inserting the surgical tool into the introducer sheath, advancing the tissue separation tip into the tissue with the separation tip being in the first configuration, placing the separation tip in the second configuration to separate the tissue with the separation tip to form a tissue gap, performing a medical procedure with the at least one surgical instrument consonant with the formation of the tissue gap, returning the separation tip to the first configuration, and further advancing the tissue separation tip into the tissue with the separation tip being in the first configuration.

The tissue separation tip may include a plurality of inflatable members which, when inflated, serve to separate the tissue and form the tissue gap and the placing step may include inflating the inflatable members. The tissue separation tip may comprise a plurality of fingers extending from and hingedly coupled to the sheath distal portion and the placing step may include opening the fingers at the distal portion of the sheath.

The tissue separation tip may comprise a plurality of fingers extending from and hingedly coupled to the sheath distal portion and a plurality of inflatable members which, when inflated, serve to separate the tissue and form the tissue gap. The placing step may include first inflating the inflatable members and thereafter opening the fingers at the distal portion of the sheath while deflating the inflatable members.

The tissue separation tip may comprise a plurality of fingers extending from and hingedly coupled to the sheath distal portion and a plurality of inflatable members which, when inflated, serve to separate the tissue and form the tissue gap. The placing step may include first inflating the inflatable members and thereafter opening the fingers at the distal end of the sheath while deflating the inflatable members and maintaining substantially constant pressure on the separated tissue.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 5 is a side view, with portions cut away, of the introducer device of FIG. 1 shown in a third configuration of use;

FIG. 6 is a side view, with portions cut away, of the introducer device of FIG. 1 during the preparation for the performance of a medical procedure while the introducer device is in the third configuration of use;

FIG. 7 is a side view, with portions cut away, showing the performance of a medical procedure while the introducer device of FIG. 1 is in the third configuration of use;

DETAILED DESCRIPTION

Figure 1:
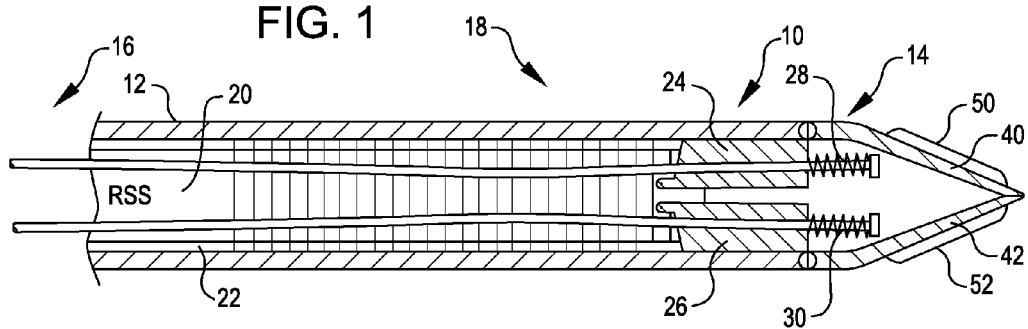
FIG. 1 is side view, with portions cut away, of an introducer device embodying the present invention in a first configuration of use.

FIG. 1 is a side view of an introducer device 10 embodying the present invention. The introducer 10 generally includes a sheath 12 and a tissue separation tip 14. The introducer has a proximal portion 16 and a distal portion 18 that includes the separation tip 14.

The sheath 12 is dimensioned for receiving a surgical tool 20 therein. The surgical tool may be, for example, the surgical device shown and described in the aforementioned co-pending application Ser. No. 12/943,745, filed Nov. 10, 2010, for SURGICAL DEVICE, which application is incorporated herein in its entirety. To that end, the surgical tool 20 includes a sheath 22. At the distal end of the sheath 20 are tool supports 24 and 26. The sheath 20 and supports 24 and 26 accommodate tool conduits 28 and 30. The conduits permits surgical instruments to be inserted into the tool 20 or removed there from during a medical procedure without requiring the entire tool 20 from being removed from the patient. As will be seen subsequently, as the introducer separates tissue to form tissue gaps, the surgical instruments may be advanced through the tool 20 and used to perform a medical procedure consonant with the formation of the tissue gap. Such procedures may include visualization, connective tissue cutting and cauterizing. Still further, once the surgical site is reached, the introducer may serve to maintain the surgical site and permit performance of work at the surgical site.

Figure 2:
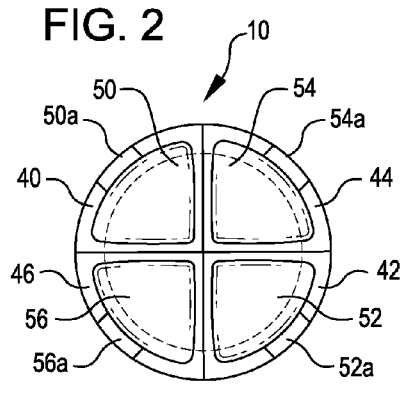
FIG. 2 is an end view of the introducer of FIG. 1.
Figure 3:
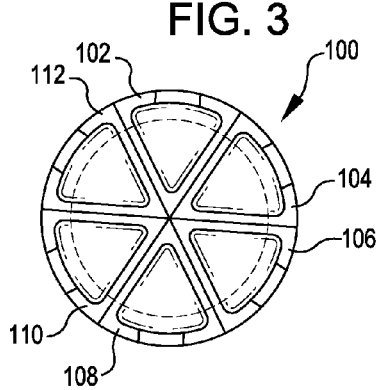
FIG. 3 is an end view showing an alternative embodiment of the introducer device of FIG. 1.

The introducer 10 includes a plurality of fingers extending from the sheath 12 in the distal direction. The number of fingers employed in the introducer may vary depending upon the circumstances. In accordance with this embodiment, and may be seen in FIG. 2, the introducer 10 includes four fingers, 40, 42, 44, and 46. The fingers are hingely connected to the distal portion 18 of the 12. Also, as may be seen in FIG. 3, the introducer 100 there shown includes six fingers, fingers 102, 104, 106, 108, 110, and 112.

The introducer 10 further comprises a like plurality of inflatable members or balloons 50, 52, 54, and 56. Each balloon is associated with and carried by one of the respective fingers 40, 42, 44, and 46. Each of the inflatable members or balloons has a conduit that provides it with inflating fluid. To that end, balloon 50 is associated with conduit 50a, balloon 52 is associated with conduit 52a, balloon 54 is associated with conduit 54a, and balloon 56 is associated with conduit 56a. All of the balloons may be inflated concurrently or in selectable groups.

The combination of the balloons and the fingers provides a positive but gentle separation of tissue during surgical tool advancement towards the surgical site. As the balloons or selected balloons or balloon groups are inflated, the tissue is first separated to form a tissue gap. Thereafter, selected fingers, selected groups of fingers, or all of the fingers are opened as the balloons are deflated. This maintains the tissue gap formed by the inflatable members while also maintaining substantially constant pressure on the separated tissue. The forgoing is illustrated in the follow sequence of FIGS. 4-7.

Figure 4:
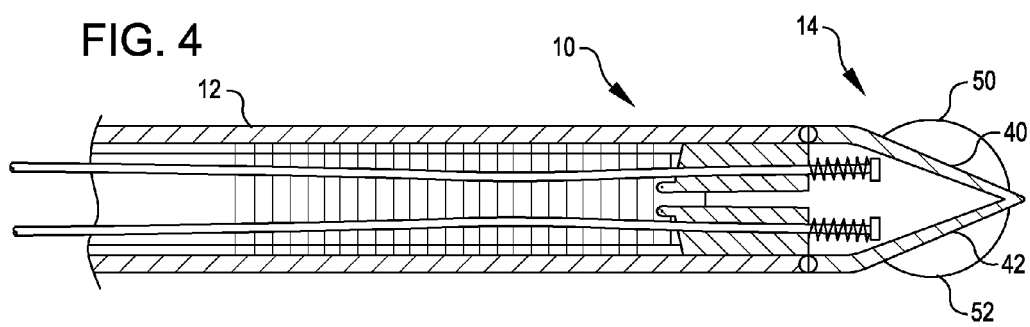
FIG. 4 is a side view, with portions cut away, of the introducer device of FIG. 1 shown in a second configuration of use.

In use, the introducer 10 in a first configuration as shown in FIG. 1 is deployed at an entry point. Then, the balloons 50, 52, 54, and 56 are inflated to gently displace and separate the tissue to form a tissue gap as shown in FIG. 4. The introducer is now in a second configuration. Next, as seen in FIG. 5, the fingers 40, 42, 44, and 46 are opened. As the fingers are opened, the balloons 50, 52, 54, and 56 are deflated. As the fingers are opened and the balloons are deflated, the tissue gap is maintained while substantially constant pressure is maintained on the separated tissue. The introducer is now in a third configuration of use.

With the introducer 10 in the third configuration of use, as seen in FIG. 5, it may be made ready for the performance of medical procedures. As seen in FIG. 5, the introducer, while in the third configuration of use, presents the separated tissue to one or more medical instruments to be employed in procedures such as visualization, connective tissue cutting and cauterizing consonant with advancement of the introducer 10. FIGS. 6 and 7 illustrate the medical procedures being performed.

Once the tissue gap has been formed and the medical procedures are completed, the process returns to placing the introducer back into the first configuration as shown in FIG. 1. The separation tip 14 may then be advanced and the foregoing procedure repeated until the surgical site is reached. Once the surgical site is reached, the introducer may be used to maintain the surgical site for the physician during the primary medical procedure.

Figure 8:
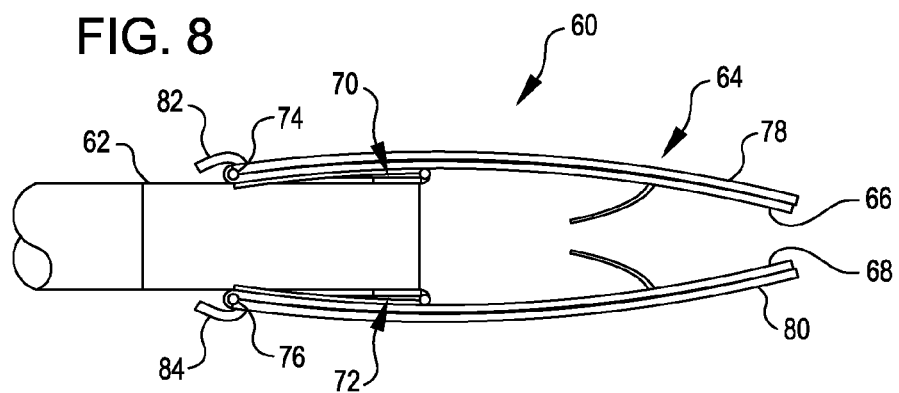
FIG. 8 is side view, with portions cut away, of another introducer device embodying the present invention in a first configuration of use.
Figure 9:
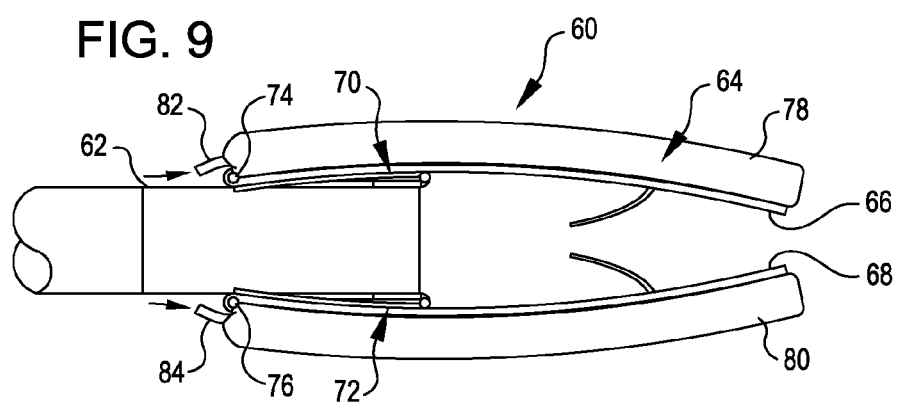
FIG. 9 is a side view, with portions cut away, of the introducer device of FIG. 8 shown in a second configuration of use.
Figure 10:
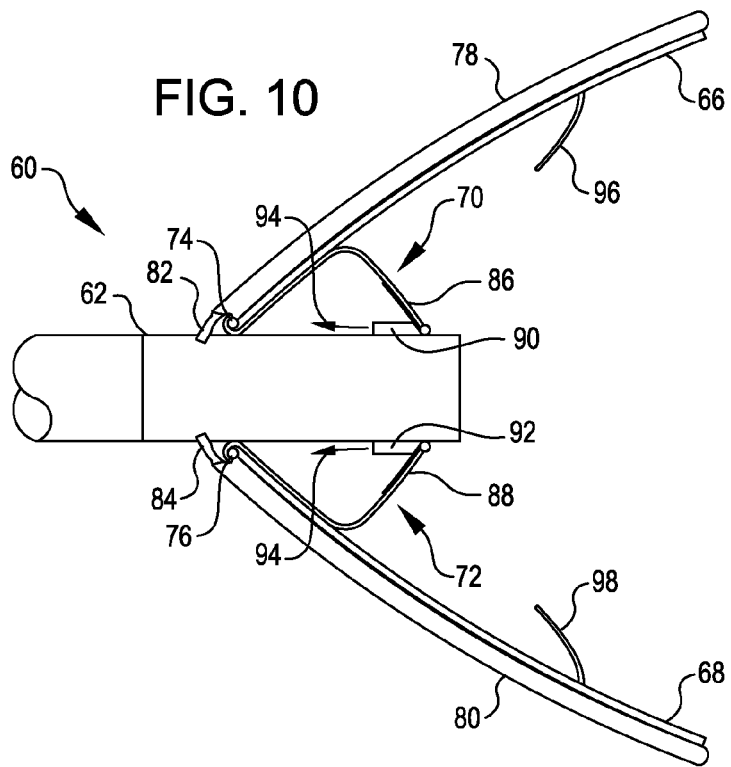
FIG. 10 is a side view, with portions cut away, of the introducer device of FIG. 8 shown in a third configuration of use.

Referring now to FIGS. 8-10, they show the distal portions of another introducer device embodying the invention. The introducer 60 includes a sheath 62 and a tissue separation tip 64. The tissue separation tip 64 includes a plurality of fingers, two of which are shown at 66 and 68. As in the previous embodiment, the device may have two or more fingers. In some embodiments, the device may have four fingers, in other embodiments six, and in other embodiments even a greater number of fingers. FIG. 8 shows the introducer in the first, closed, configuration. Each finger is associated with an actuator for opening the finger. In FIG. 8, for example, finger 66 is associated with actuator 70 and finger 68 is associated with actuator 72. The actuators are hingedly carried on the sheath in the distal portion of the sheath 62. As may be noted in FIG. 8. finger 66 is connected to the sheath distal portion by a hinge 74 and finger 68 is connected to the sheath distal portion by a hinge 76. The manner in which the actuators open the fingers will be described in detail subsequently. The introducer 60, when in the first configuration as shown in FIG. 8 is ready to be placed at an entry site or to be advance further into tissue.

As in the previous embodiment, the introducer 60 further includes a plurality of inflatable members. In accordance with this embodiment, each finger is associated with and carries an inflatable member. To that end, finger 66 carries inflatable member 78 and finger 68 carries inflatable member 80. FIG. 9 shows the introducer 60 in the second configuration with the inflatable members 78 and 80 inflated. As in the previous embodiment, as the inflatable members are inflated, adjacent tissue is gently separated or displaced. Each inflatable member 78 and 80 is associated with a conduit 82 and 84 respectively. The conduits permit the inflatable members to be filled with an inflating fluid, such as saline. The conduits may be arranged to inflate each inflatable member individually, or arranged to inflate the conduits in selective groups. The inflatable members or groups of inflatable members may be inflated concurrently or in any desired order or as required.

Figure 13:
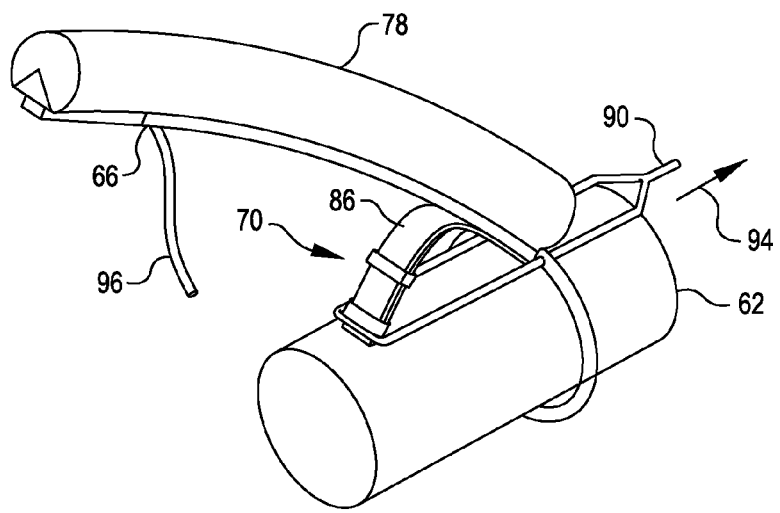
FIG. 13 is a perspective view showing details of the actuator 70 of the introducer device of FIG. 10.

FIG. 10 shows the introducer 60 in its open or third configuration. To open each finger, each finger is associated with an actuator. Finger 66 is associated with actuator 70 and finger 68 is associated with actuator 72. As previously mentioned, the fingers are each hingedly connected to the sheath 62. Actuator 70 causes finger 66 to open about hinge 74 and actuator 72 causes finger 68 to open about hinge 76. Each actuator includes a spring member that acts upon its respective finger to open the finger. Actuator 70 includes spring member 86 and actuator 72 includes spring member 88. The springs are biased to maintain contact with its finger. However, when the ends of the spring members are pulled back, the springs bow. This forces the fingers to open. More specifically, spring member 86 is connected to a control cable 90 and spring member 88 is connected to a control cable 92. Control cable 90 is shown in greater detail in FIG. 13. Here, it may be seen that the cable 90 loops around the spring member 86 and is once again connected to itself. When the cables 90 and 92 are pulled in direction of arrow 94, the spring members 86 and 88 bow out and push on their respective finger 66 and 68. As a result, fingers 66 and 68 are opened.

Figure 11:
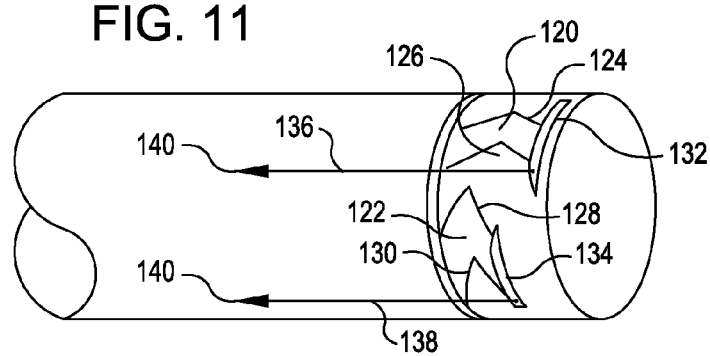
FIG. 11 is a simplified perspective view illustrating the manner in which the introducer devices may be configured for selective actuation in accordance with further aspects of the present invention.

The spring members may be acted upon by the control cables concurrently for concurrently opening the fingers. Also, the spring members may be acted upon by the control cables individually in any desired or required order to open individual fingers completely or by varying amounts. Alternatively, the spring members may be acted upon to open the fingers in groups. This is shown, for example in FIG. 11. In this simplified drawing, the spring members are arranged in groups, group 120 and group 122. Group 120 includes spring members 124 and 126. Group 122 includes spring members 128 and 130. The springs of the spring member groups are connected together by a common connector. Common connector 132 is connected to spring members 124 and 126 and common connector 134 is connected to spring members 128 and 130. Each connector is connected to a control cable. Connector 132 is connected to control cable 136 and connector 134 is connected to control cable 138. When the control cables are pulled in the direction of arrows 140, the spring members of each group are bowed together, causing the respective fingers to open together. Hence, the pulling of control cable 136 bows spring members 124 and 126 together and the pulling of control cable 138 causes spring members 128 and 130 to bow together. The groups of fingers may be opened concurrently or in a sequence as desired or required.

Returning now to FIG. 10, each of the fingers 66 and 68 is associated with a retraction cable 96 and 98. The retraction cable may be employed, if necessary, to close the fingers 66 and 68 respectively. In actual practice, the fingers may be closed by the force of tissue. However, when needed, the retraction cables 96 and 98 may be relied upon to close their respective fingers.

As in the previous embodiment, it is contemplated that as each finger 66 and 68 is opened, the corresponding inflatable member or balloon 78 and 80 is deflated. The deflation of the balloons as the fingers open serves to maintain the tissue separation or tissue gap while also maintaining a substantially constant pressure on the separated tissue.

The introducer 60 as shown in FIG. 10 presents the tissue gap or surgical site to the one or more instruments that may be received by the sheath 62. The device as described in the aforementioned co-pending application is preferably received by the sheath 62 and used to steer the introducer. Hence while the surgical device within the sheath performs the steering function, the introducer enabled the advancement of the assembly.

Figure 12:
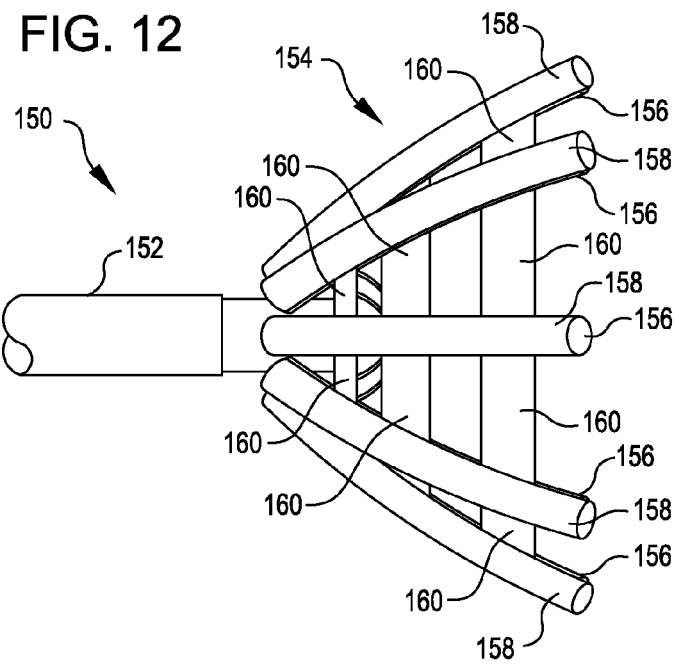
FIG. 12 is a side view of a still another introducer device embodying the present invention.

Referring now to FIG. 12, it shows another introducer device embodying the invention. The device 150 includes a sheath 152 and a tissue separation tip 154. As in the previous embodiments, the tissue separation tip includes a plurality of fingers 156 and a like plurality of inflatable members 158 carried by the fingers 158. Between the fingers 158 is a web 160. The web provides substantially uniform support for the separated tissue when the introducer is in the third configuration of FIG. 10. As may be appreciated by those skilled in the art, the web may also be employed in the embodiments of FIGS. 8-11 for providing substantially uniform support for the separated tissue. Further, the embodiments of FIGS. 1-7 may also include control cables for opening and closing the fingers. The control cables may extend proximally along the introducer sheath in a manner similar to the control cables of the surgical device of co-pending application Ser. No. 12/943,745, for connection to a control assembly.

In each embodiment disclosed herein, the sheath may be compositely formed of one or more flexible materials such as, for example, PVDF (polyvinylidene flouride), Nylon (Polyamide), Polyethylene terephthalate (PET), or polycarbonate. Similarly, the fingers and actuators may be compositely formed of one or more flexible material such as, for example, Nitinol (Nickel Titanium), spring steel, stainless steel, titanium, PVDF (polyvinylidene flouride), Nylon (Polyamide), Polyethylene terephthalate (PET), or polycarbonate. Such materials are well known in the art.

While a particular embodiment of the invention has been shown and described, changes and modifications may be made. It is therefore intended to cover in the appended claims all such changes and modifications which fall within the true spirit and scope of the invention.

What is claimed is:

1. An introducer for providing a surgical tool with a pathway through tissue to a surgical site, wherein the surgical tool includes at least one surgical instrument, the introducer comprising:

a flexible sheath having a distal portion including a distal end and configured to receive the surgical tool;

a tissue separation tip coupled with the distal portion of the sheath for advancing the sheath into the tissue towards the surgical site, the tissue separation tip being configured to separate tissue to form a tissue gap and provide the at least one surgical instrument access to the tissue gap for performing a medical procedure consonant with the formation of the tissue gap or the performance of work at the surgical site, the tissue separation tip including a plurality of fingers and a corresponding plurality of inflatable members, each of the fingers extending from and hingedly coupled with the sheath distal portion and carrying a respective one of the inflatable members, which, when inflated, serve to separate the tissue and form the tissue gap;

one or more conduits coupled with the inflatable members to transfer an inflating fluid to and from the inflatable members; and one or more actuators operatively coupled with the fingers to open the fingers, wherein the inflatable members and the fingers are configured such that, during a reconfiguration from a first configuration in which the inflatable members are inflated and the fingers are in a closed configuration to a second configuration in which the inflatable members are fully deflated and the fingers are in an open configuration in which the fingers are oriented substantially parallel to the distal portion of the sheath, substantially constant pressure can be maintained on the separated tissue so as to maintain the tissue gap.

2. The introducer of claim 1 wherein the plurality of fingers are configured to be advanced into the tissue in the closed configuration.

3. The introducer of claim 2, wherein the plurality of fingers comprise at least two fingers.

4. The introducer of claim 2, further comprising a control cable associated with each finger.

5. The introducer of claim 2, further comprising a retraction cable associated with each finger.

6. The introducer of claim 2, wherein the one or more actuators comprise an actuator associated with each finger, the one or more actuators being configured such that each finger is actuated individually.

7. The introducer of claim 2, wherein the one or more actuators comprise an actuator associated with each finger, the one or more actuators being configured such that the fingers are opened concurrently.

8. The introducer of claim 2, wherein the one or more actuators comprise an actuator associated with each finger, the one or more actuators being operative in groups of two or more for opening different groups of the fingers by different amounts.

9. The introducer of claim 2, further comprising webbing bridging adjacent fingers to apply substantially uniform distributed pressure on the separated tissue.

10. The introducer of claim 1, wherein each of the inflatable members is individually inflated.

11. The introducer of claim 1, wherein the inflatable members are concurrently inflated.

12. The introducer of claim 1, wherein each of at least two selected groups of two or more of the inflatable members is separately inflated.

13. The introducer of claim 1, further comprising a control cable for opening the fingers.

14. The introducer of claim 1, further comprising a retraction cable for closing the fingers.

15. The introducer of claim 1, further comprising a plurality of retraction cables, the retraction cables being configured for the individual closing of the fingers.

16. The introducer of claim 1, further comprising a plurality of retraction cables, the retraction cables being configured for closing the fingers in selectable groups of two or more for concurrent closing of selected groups of fingers by differing amounts.

17. The introducer of claim 1, wherein the one or more actuators comprise an actuator associated with each finger, the one or more actuators being configured such that each finger is actuated individually.

18. The introducer of claim 1, wherein the one or more actuators comprise an actuator associated with each finger, the one or more actuators being configured such that the fingers are opened concurrently.

19. The introducer of claim 1, wherein the one or more actuators comprise an actuator associated with each finger, the one or more actuators being operative in groups of two or more for opening different groups of the fingers by different amounts.

20. The introducer of claim 1, further comprising a webbing bridging adjacent fingers to apply uniform distributed pressure on the separated tissue.

21. The introducer of claim 1, wherein at least one of the inflatable members, when inflated, has a substantially convex outer surface that engages the tissue to form the tissue gap.

22. The introducer of claim 1, wherein each of the inflatable members, when inflated, has a substantially convex outer surface that engages the tissue to form the tissue gap.

23. An introducer for providing a surgical tool with a pathway through tissue to a surgical site, the introducer comprising:
  an elongated flexible sheath configured to receive the surgical tool therein;
  a tissue separation tip supported by the sheath and configured to separate tissue to form a tissue gap and provide the surgical tool access to the tissue gap, the tissue separation tip including a plurality of fingers and a corresponding plurality of inflatable members, each of the fingers extending from and hingedly coupled with the sheath and carrying a respective one of the inflatable members, which, when inflated, serve to separate the tissue and form the tissue gap;
  one or more conduits coupled with the inflatable members to transfer an inflating fluid to and from the inflatable members; and
  one or more actuators operatively coupled with the fingers to open the fingers, wherein the inflatable members and the fingers are configured such that, during a reconfiguration from a first configuration in which the inflatable members are inflated and the fingers are in a closed configuration to a second configuration in which the inflatable members are fully deflated and the fingers are in an open configuration in which the fingers are oriented substantially parallel to the distal portion of the sheath, substantially constant pressure can be maintained on the separated tissue so as to maintain the tissue gap.

* * * * *